US012797097B2

(12) United States Patent
Mustafa et al.

(10) Patent No.: US 12,797,097 B2
(45) Date of Patent: Nov. 17, 2026

(54) RETRIEVAL CATHETER

(71) Applicant: CERETRIEVE LTD., Yokneam Illit (IL)

(72) Inventors: Maysa Mustafa, Zichron Yaakuv (IL); Maxim Vasylevytsky, Kefar-Sava (IL); Aviram Alfia, Karmiel (IL); Amir Belson, Savyon (IL)

(73) Assignee: CERETRIEVE LTD., Yokneam Illit (IL)

( * ) Notice: Subject to any disclaimer, the term of this patent is extended or adjusted under 35 U.S.C. 154(b) by 36 days.

(21) Appl. No.: 18/973,438

(22) Filed: Dec. 9, 2024

(65) Prior Publication Data

US 2025/0099122 A1 Mar. 27, 2025

Related U.S. Application Data

(63) Continuation-in-part of application No. PCT/IL2023/050643, filed on Jun. 21, 2023.

(Continued)

(51) Int. Cl.

*A61B 17/221* (2006.01)
*A61B 17/00* (2006.01)

(52) U.S. Cl.

CPC ...... *A61B 17/221* (2013.01); *A61B 17/00234* (2013.01); *A61B 2017/00238* (2013.01);

(Continued)

(58) Field of Classification Search

CPC .......... A61F 2/01; A61F 2/0105; A61F 2/011; A61F 2/013; A61F 2002/16; A61F 2/90;

(Continued)

(56) References Cited

U.S. PATENT DOCUMENTS 4,611,594 A 9/1986 Grayhack et al.
5,275,605 A 1/1994 Winkler (Continued)

FOREIGN PATENT DOCUMENTS

CN 107205751 A 9/2017
EP 2288311 A2 3/2011

(Continued)

OTHER PUBLICATIONS

PCT International Search Report for International Application No. PCT/IL2023/050643, mailed Sep. 11, 2023, 3pp.

(Continued)

*Primary Examiner* — Majid Jamialahmadi
(74) *Attorney, Agent, or Firm* — The Roy Gross Law Firm, LLC; Roy D. Gross

(57) ABSTRACT

An apparatus for removing an obstruction from a blood vessel of a subject comprises a flexible catheter and a trap. The trap is formed from a set of braided wires covered in a covering, and, at a distal end of the trap, has an oval opening that is beveled such that the oval opening has a distal portion, and a proximal portion proximal from the distal portion. The trap has a beak, defined by wires of the set, that extends over the proximal portion of the oval opening. The trap is biased to assume an expanded state in which the oval opening is wider than a rim of the catheter, and is compressible into a compressed state within the catheter such that the oval opening is narrower than in the expanded state. Other embodiments are also described.

21 Claims, 7 Drawing Sheets

Related U.S. Application Data

(60) Provisional application No. 63/355,111, filed on Jun. 24, 2022.

(52) U.S. Cl.
CPC ............... *A61B 2017/00305* (2013.01); *A61B 2017/00389* (2013.01); *A61B 2017/00831* (2013.01); *A61B 2017/2215* (2013.01)

(58) Field of Classification Search
CPC ....... A61F 2002/821; A61F 2230/0008; A61B 17/221; A61B 2017/2212; A61B 2017/2215; A61B 2017/2217; A61B 2017/00358; A61B 2017/00867
See application file for complete search history.

(56) References Cited

U.S. PATENT DOCUMENTS

| | | | |
|---|---|---|---|
| 5,653,684 | A | 8/1997 | Laptewicz et al. |
| 6,695,858 | B1 | 2/2004 | Dubrul et al. |
| 6,893,451 | B2 | 5/2005 | Cano et al. |
| 7,727,243 | B2 | 6/2010 | Sepetka et al. |
| 8,585,713 | B2 | 11/2013 | Ferrera et al. |
| 8,795,305 | B2 | 8/2014 | Martin et al. |
| 8,900,179 | B2 | 12/2014 | Jenson et al. |
| 9,155,552 | B2 | 10/2015 | Ulm, III |
| 9,427,244 | B2 | 8/2016 | Lund-Clausen et al. |
| 10,130,379 | B2 | 11/2018 | Welch et al. |
| 10,179,224 | B2 | 1/2019 | Yang et al. |
| 10,682,152 | B2 | 6/2020 | Vale et al. |
| 10,792,056 | B2 | 10/2020 | Vale et al. |
| 11,013,523 | B2 | 5/2021 | Arad Hadar |
| 11,241,244 | B2 | 2/2022 | Jaffe et al. |
| 11,344,325 | B2 | 5/2022 | Harari et al. |
| 11,446,045 | B2 | 9/2022 | Vale et al. |
| 11,534,191 | B2 | 12/2022 | Fàbrega et al. |
| 11,766,539 | B2 | 9/2023 | Yee et al. |
| 2001/0051810 | A1 | 12/2001 | Dubrul et al. |
| 2002/0072764 | A1 | 6/2002 | Sepetka et al. |
| 2002/0161393 | A1 | 10/2002 | Demond et al. |
| 2003/0078519 | A1 | 4/2003 | Salahieh et al. |
| 2003/0176884 | A1 | 9/2003 | Berrada et al. |
| 2003/0195537 | A1 | 10/2003 | Dubrul et al. |
| 2004/0122468 | A1 | 6/2004 | Yodfat et al. |
| 2005/0085826 | A1 | 4/2005 | Nair et al. |
| 2005/0228417 | A1 | 10/2005 | Teitelbaum et al. |
| 2006/0030865 | A1 | 2/2006 | Balg |
| 2006/0047286 | A1 | 3/2006 | West |
| 2006/0116659 | A1 | 6/2006 | Wahr et al. |
| 2006/0155305 | A1 | 7/2006 | Freudenthal et al. |
| 2006/0195118 | A1 | 8/2006 | Richardson et al. |
| 2006/0195137 | A1 | 8/2006 | Sepetka et al. |
| 2009/0192485 | A1 | 7/2009 | Heuser |
| 2010/0030256 | A1 | 2/2010 | Dubrul et al. |
| 2012/0041419 | A1 | 2/2012 | Blanchard et al. |
| 2012/0041449 | A1 | 2/2012 | Eckhouse et al. |
| 2012/0041474 | A1 | 2/2012 | Eckhouse et al. |
| 2012/0277788 | A1* | 11/2012 | Cattaneo .................. A61F 2/90 606/200 |
| 2013/0079796 | A1 | 3/2013 | Slee et al. |
| 2014/0171958 | A1 | 6/2014 | Baig |
| 2014/0257362 | A1 | 9/2014 | Eidenschink |
| 2014/0309655 | A1 | 10/2014 | Gal et al. |
| 2016/0310255 | A1 | 10/2016 | Purcell et al. |
| 2017/0215900 | A1* | 8/2017 | Lowinger ........... A61B 17/221 |
| 2018/0193026 | A1 | 7/2018 | Yang et al. |
| 2018/0235743 | A1 | 8/2018 | Farago et al. |
| 2019/0274810 | A1 | 9/2019 | Phouasalit et al. |
| 2019/0298396 | A1 | 10/2019 | Gamba et al. |
| 2020/0009301 | A1 | 1/2020 | Yee |
| 2020/0138460 | A1 | 5/2020 | Yang et al. |
| 2020/0297972 | A1 | 9/2020 | Yee et al. |
| 2021/0059695 | A1 | 3/2021 | Harari et al. |
| 2021/0077134 | A1 | 3/2021 | Vale et al. |
| 2021/0106238 | A1 | 4/2021 | Strasser et al. |
| 2021/0154433 | A1 | 5/2021 | Casey et al. |
| 2021/0154443 | A1 | 5/2021 | Casey |
| 2021/0177427 | A1 | 6/2021 | Nguyen et al. |
| 2021/0186537 | A1 | 6/2021 | Buck et al. |
| 2021/0186542 | A1 | 6/2021 | Buck et al. |
| 2021/0187244 | A1 | 6/2021 | Buck et al. |
| 2021/0315596 | A1 | 10/2021 | Buck et al. |
| 2021/0315597 | A1 | 10/2021 | Buck et al. |
| 2021/0315598 | A1 | 10/2021 | Buck et al. |
| 2021/0316121 | A1 | 10/2021 | Buck et al. |
| 2021/0316127 | A1 | 10/2021 | Buck et al. |
| 2022/0047849 | A1 | 2/2022 | Yee et al. |
| 2022/0117614 | A1 | 4/2022 | Salmon et al. |
| 2022/0330960 | A1 | 10/2022 | Buck et al. |
| 2022/0331085 | A1 | 10/2022 | Buck et al. |
| 2022/0331509 | A1 | 10/2022 | Buck et al. |
| 2022/0354517 | A1 | 11/2022 | Behan |
| 2023/0015259 | A1 | 1/2023 | Buck et al. |
| 2023/0048055 | A1 | 2/2023 | Lau |
| 2023/0061728 | A1 | 3/2023 | Davis et al. |
| 2023/0072403 | A1 | 3/2023 | Strasser et al. |
| 2023/0127145 | A1 | 4/2023 | Arad Hadar et al. |
| 2023/0132996 | A1* | 5/2023 | Stefanov .............. A61B 17/221 606/159 |
| 2023/0211122 | A1 | 7/2023 | Luna et al. |
| 2024/0032949 | A1 | 2/2024 | Yang et al. |
| 2024/0033016 | A1 | 2/2024 | Yang et al. |
| 2024/0033018 | A1 | 2/2024 | Yang et al. |
| 2024/0033019 | A1 | 2/2024 | Lau et al. |
| 2024/0033486 | A1 | 2/2024 | Lau et al. |
| 2024/0042124 | A1 | 2/2024 | Bartholomew |
| 2024/0042142 | A1 | 2/2024 | Bartholomew et al. |

FOREIGN PATENT DOCUMENTS

| | | | |
|---|---|---|---|
| EP | 2578184 | A1 | 4/2013 |
| EP | 3335647 | A2 | 6/2018 |
| EP | 3990083 | A1 | 5/2022 |
| ES | 2577288 | A1 | 7/2016 |
| JP | 7017408 | B2 | 2/2022 |
| WO | 2001008742 | A1 | 2/2001 |
| WO | 2001008743 | A1 | 2/2001 |
| WO | 2002011627 | A2 | 2/2002 |
| WO | 2002056797 | A2 | 7/2002 |
| WO | 2002094111 | A2 | 11/2002 |
| WO | 2003009781 | A1 | 2/2003 |
| WO | 2003032868 | A1 | 4/2003 |
| WO | 2009076482 | A1 | 6/2009 |
| WO | 2010017537 | A2 | 2/2010 |
| WO | 2016010995 | A1 | 1/2016 |
| WO | 2016/113047 | A1 | 7/2016 |
| WO | 2016/126974 | A1 | 8/2016 |
| WO | 2017072663 | A1 | 5/2017 |
| WO | 2017072761 | A1 | 5/2017 |
| WO | 2017097616 | A1 | 6/2017 |
| WO | 2017/147493 | A1 | 8/2017 |
| WO | 2019064306 | A1 | 4/2019 |
| WO | 2019212984 | A1 | 11/2019 |
| WO | 2019213179 | A1 | 11/2019 |
| WO | 2020/010310 | A1 | 1/2020 |
| WO | 2020079082 | A1 | 4/2020 |
| WO | 2020099386 | A1 | 5/2020 |
| WO | 2020/144071 | A1 | 7/2020 |
| WO | 2020/260632 | A1 | 12/2020 |
| WO | 2021016213 | A1 | 1/2021 |
| WO | 2021067264 | A1 | 4/2021 |
| WO | 2021076642 | A1 | 4/2021 |
| WO | 2021127004 | A1 | 6/2021 |
| WO | 2021183444 | A1 | 9/2021 |
| WO | 2021263033 | A1 | 12/2021 |
| WO | 2022028831 | A1 | 2/2022 |
| WO | 2022028833 | A1 | 2/2022 |
| WO | 2022035867 | A1 | 2/2022 |
| WO | 2022055810 | A1 | 3/2022 |
| WO | 2022123565 | A1 | 6/2022 |
| WO | 2022180083 | A1 | 9/2022 |
| WO | 2022180084 | A1 | 9/2022 |
| WO | 2023019118 | A1 | 2/2023 |

(56) References Cited

FOREIGN PATENT DOCUMENTS

| | | | |
|---|---|---|---|
| WO | 2023019122 | A1 | 2/2023 |
| WO | 2023034375 | A1 | 3/2023 |
| WO | 2023044231 | A1 | 3/2023 |
| WO | 2023069874 | A1 | 4/2023 |
| WO | 2023091762 | A1 | 5/2023 |
| WO | 2023117159 | A1 | 6/2023 |
| WO | 2023117919 | A1 | 6/2023 |
| WO | 2023159063 | A2 | 8/2023 |
| WO | 2023220707 | A2 | 11/2023 |
| WO | 2023248224 | A1 | 12/2023 |
| WO | 2024020506 | A2 | 1/2024 |
| WO | 2024030368 | A2 | 2/2024 |
| WO | 2024030405 | A2 | 2/2024 |

OTHER PUBLICATIONS

PCT Written Opinion for International Application No. PCT/IL2023/050643, mailed Sep. 11, 2023, 5pp.

PCT International Search Report for International Application No. PCT/IL2021/051461, mailed Mar. 24, 2022, 3pp.

PCT Written Opinion for International Application No. PCT/IL2021/051461, mailed Mar. 24, 2022, 9pp.

PCT International Search Report for International Application No. PCT/IL2018/051074, mailed Jan. 13, 2019, 3pp.

PCT Written Opinion for International Application No. PCT/IL2018/051074, mailed Jan. 13, 2019, 7pp.

United States Patent and Trademark Office, Non-Final Office Action for U.S. Appl. No. 18/615,413, mailed Oct. 31, 2024, 17pp.

United States Patent and Trademark Office, Non-Final Office Action for U.S. Appl. No. 17/731,423, mailed Sep. 7, 2023, 17pp.

United States Patent and Trademark Office, Non-Final Office Action for U.S. Appl. No. 16/644,244, mailed Jun. 23, 2021, 21pp.

* cited by examiner 10
14
16
26
24
25
20
18
22
12
40
42
44
46,48
(I)
(II)
228
226

RETRIEVAL CATHETER

CROSS-REFERENCES TO RELATED APPLICATIONS

The present application is a Continuation-in-Part of International Patent Application PCT/IL2023/050643 to Mustafa et al., filed 21 Jun. 2023, titled "Retrieval catheter," which published as WO 2023/248224, and which claims priority from Provisional U.S. Patent Application 63/355,111 to Mustafa et al., filed 24 Jun. 2022, and titled "Retrieval catheter." Each of the above applications is incorporated herein by reference in its entirety.

BACKGROUND

The present invention relates to a catheter for retrieving material or objects from a biological vessel and to a system and method of using same. Embodiments of the present invention relate to a thrombus-trapping catheter configured for suction-assisted retrieval that is configured capable of compensating for trap collapse during suction. Vascular diseases caused by blockages of blood vessels are a leading cause of mortality and morbidity in the United States.

A brain embolism is a blockage in a blood vessel within the brain or in an artery that supplies blood to the brain. Blockages can be caused by a blood clot, fat globule, or air pocket within an artery. A brain embolism causes an embolic stroke that in 2020 accounted for 1 in 6 deaths from vascular disease in the United States.

Interventional procedures are routinely used to treat vascular diseases and are particularly advantageous for treating vascular blockages located in small and remote vessels such as those within the brain.

Minimally invasive retrieval of a brain embolus is typically carried out using a retrieval catheter designed for capturing and retrieving the embolus using a mechanical trap and/or suction.

Although such retrieval devices can be effective in retrieving small clots, retrieval of large clots using suction can lead to trap collapse due to plugging of the trap opening by the clot material. Such collapse oftentimes results in incomplete clot retrieval and clot fragmentation.

In order to traverse these limitations of suction-assisted clot retrieval, operators oftentimes disconnect the source of suction (syringe or pump) to reverse collapse and then reapply suction in order to attempt to retrieve the clot or completely withdraw the system from the vasculature to unplug the trap and repeat the procedure.

Thus, there is still room for improvement in clot retrieval systems and in particular in the complete retrieval capabilities of systems utilizing suction.

SUMMARY

According to one aspect of the present invention there is provided a system for retrieving material or objects from a biological vessel comprising a catheter having an outer tube covering an elongated trap, wherein a lumen of the outer tube forms a conduit for applying a suctioning force to a distal opening of the elongated trap when the elongated trap is deployed from the outer tube.

According to embodiments of the present invention when deployed out of the outer tube a proximal portion of the elongated trap forms a fluid tight seal with an inner wall of the outer tube.

According to embodiments of the present invention the proximal portion is externally coated with a polymer capable of maintaining the fluid tight seal.

According to embodiments of the present invention the elongated trap is formed from a braid structure that is capable of radial expansion or elongation when deployed.

According to embodiments of the present invention the braid structure is internally coated with a polymer.

According to embodiments of the present invention a distal portion of the outer tube is more flexible than a proximal portion thereof.

According to embodiments of the present invention the outer tube includes a wire braid at the proximal portion.

According to embodiments of the present invention the outer tube includes a wire spiral at the distal portion.

According to embodiments of the present invention when radially expanded, the coated braid structure is conical with a beveled distal end.

According to embodiments of the present invention the system further comprises a probe positionable within the elongated trap, the probe being for identifying a presence of the material or object within the elongated trap.

According to embodiments of the present invention the probe includes a radiopaque marker.

According to embodiments of the present invention the system further comprises a pressure probe.

According to embodiments of the present invention the pressure probe is a strain sensor.

According to embodiments of the present invention the system further comprises a rod or wire for moving the braid structure against the outer tube.

According to embodiments of the present invention the rod or the wire are positioned within a channel attached to, or formed in a wall of the outer tube.

According to embodiments of the present invention the elongated trap includes a beveled opening at a proximal end thereof.

According to embodiments of the present invention the wire or rod is attached to a side of the beveled opening.

According to embodiments of the present invention the system further comprises a source of suction fluidly connected to the outer tube.

According to embodiments of the present invention the system further comprises an element for restricting a bend radius of the braid structure along a longitudinal axis thereof.

According to embodiments of the present invention the element is a strut interconnecting the braid structure and the wire or rod.

According to embodiments of the present invention the element is designed to limit a bend radius of the braid structure to 1 mm or more.

According to embodiments of the present invention the system further comprises a suction source connected to the lumen of the outer tube, a pressure sensor for sensing a pressure in the lumen or the elongated trap and a control unit for controlling a pressure of the suction source.

According to embodiments of the present invention the control unit can automatically decrease a pressure applied by the suction source to the lumen when the sensor detects a rise in the pressure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1C illustrates the trap collapsed within the catheter tube showing the beveled proximal end and deployment rod.

FIG. 3B illustrates an integral flexible tube interface to be connected to the trap and the rod-trap interface (FIGS. 3C-D).

DETAILED DESCRIPTION

Figures 1A, 1B, 1C:
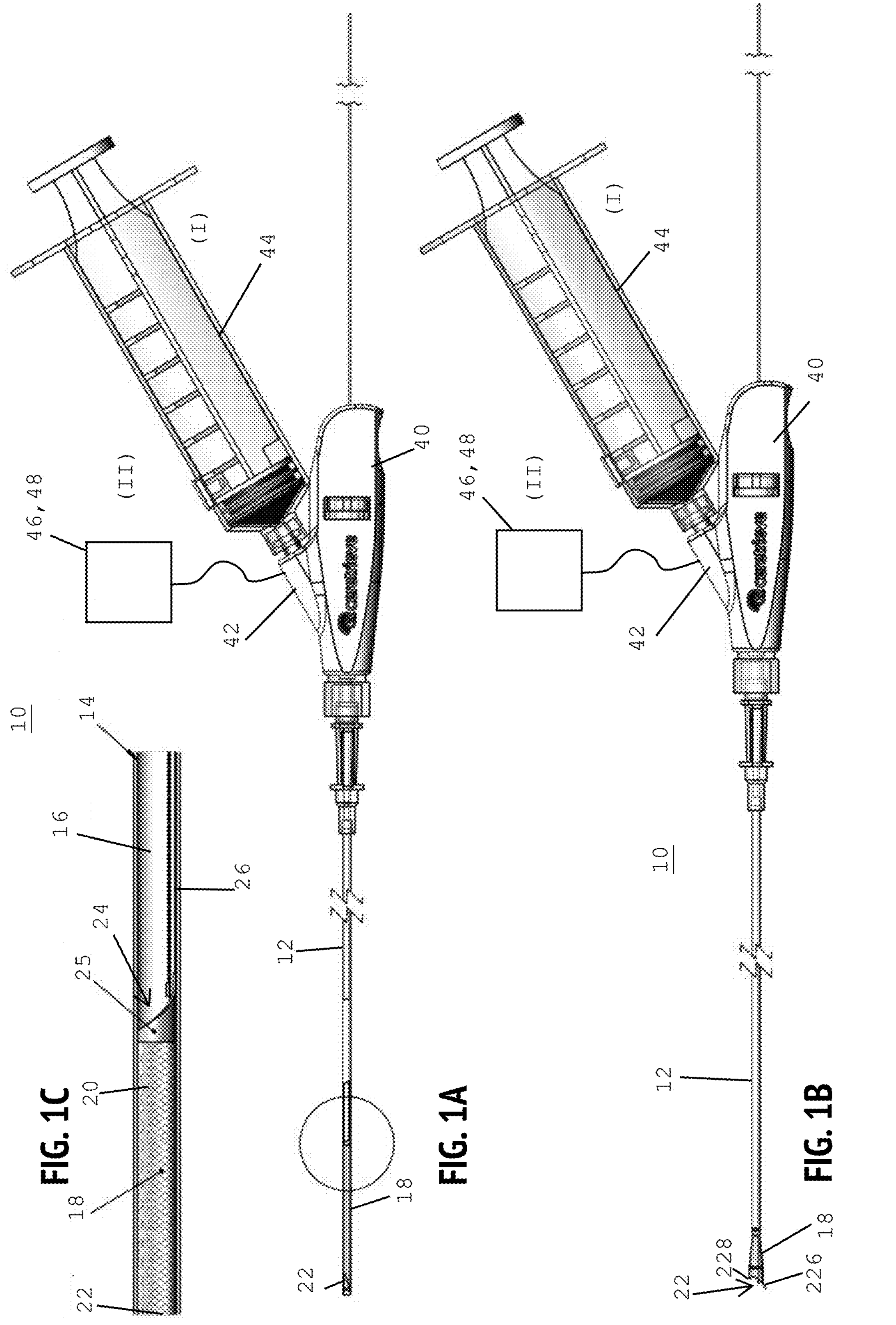
FIGS. 1A-C illustrate an embodiment of the present system showing the catheter connected to a syringe (I) or a pump and control unit (II) with the trap sequestered within the catheter tube (FIG. 1A) or deployed therefrom (FIG. 1B).

The present invention is of a catheter, system and method that can be used to retrieve material/objects such as clots, emboli and the like from a biological vessel such as a blood vessel in the brain.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Catheters for trapping and extracting thrombus material are well known in the art. Such catheters use a suctioning force to engulf and trap embolic material and remove it from the body.

One problem often encountered with such devices is the collapse of the trap under suction due to plugging of the distal opening of the trap. Under such conditions, the physician oftentimes needs to withdraw the system, unplug it and repeat the procedure.

While reducing the present invention to practice, the present inventors experimented with several catheter designs in efforts of minimizing or compensating for such collapse.

Thus, according to one aspect of the present invention there is provided a catheter system for retrieval of material or object from a biological vessel.

As used herein, the term “material” refers to a biological material such as that characterizing a thrombus/embolus while the term “object” refers to an implant such as a stent, stent-graft and the like.

Any biological vessel can be accessed and treated using the present system, examples include vessels of the circulatory system (e.g., arteries, veins, lymph vessels), vessels of the urinary tract (e.g., urethra, ureters) and vessels of the lymphatic system. The present catheter system is particularly suitable for use in brain vessels (veins arteries).

The system of the present invention includes a catheter 12 attached to an elongated trap 18 configured for deployment from a lumen 16 of the catheter (the trap capable of forming a tube-like or conical sleeve when deployed). When deployed out of the catheter lumen (by advancing the trap out of the catheter and/or pulling the catheter to unsheathe the trap), the shape of the elongated trap is determined by the diameter of the vessel. That is, trap 18 is biased to assume an expanded state in which a distal opening 22 is wider than a catheter-rim 121, and is elastically compressible into a compressed state within lumen 16 in which the distal opening is narrower than in the expanded state.

In cases where the trap is expanded in vessels that are smaller than the catheter outer diameter, the trap assumes a tube-like shape. When expanded in vessels larger than the diameter of the catheter, the trap assumes a conical shape that tapers in diameter from the distal to the proximal end. The elongated trap can be a coated braid structure that is self-expanding in which case, at least a portion of which will self-expand to a final diameter that is limited by a diameter of the vessel (and up to a diameter limited by the braid structure and the extent of deployment from the catheter sheath). Trap 18 can thus be funnel-shaped and act like a funnel, e.g., by funneling the embolus proximally therethrough.

The elongated trap 18 includes a lumen 19 that is open at both distal and proximal ends, thereby defining a distal opening 22 and a proximal opening 24. The distal end opening 22 can be beveled, i.e., circular or ovular in shape and perpendicular to the longitudinal axis of the catheter and tilted/angled (oblique) with respect to the longitudinal axis of the catheter (also referred to herein as a “shovel configuration”). As shown, distal opening 22 can define a shovel 226 that protrudes outwardly and obliquely to a longitudinal axis of the catheter, e.g., thereby being adapted to “scoop” up an embolus. Shovel 226 may be defined by, or extend away from, a distal portion 221 of the oval. In some implementations, distal opening 22 has a beak 228 (e.g., an opposing shovel), defined by wires of the trap that extend over proximal portion 227 of the oval opening. In some implementations, beak 228 can be considered a first beak, and shovel 226 can be considered a second beak, e.g., the wires that define trap 18 may be arranged at the distal portion 221 such that, at the distal end of shovel 226, they flare outwardly and away from the longitudinal axis of the trap, and optionally flaring away from the ovular opening. In some implementations, shovel 226 is defined by wire loops.

Opposing shovel 228 may protrude distally (e.g. from distal opening 22), but is typically shorter than shovel 226 (such that shovel 226 protrudes distally beyond the opposing shovel).

As shown, first shovel 226 meets opposing shovel 228 (e.g., beak) at exactly two commissures 282. Commissures 282 are disposed proximally to a distal end of each of shovels 226 and 228. That is, distal opening is comprised of exactly two protrusions, first shovel 226, and opposing shovel 228, with exactly two proximal commissures 282 therebetween.

Figure 3A:
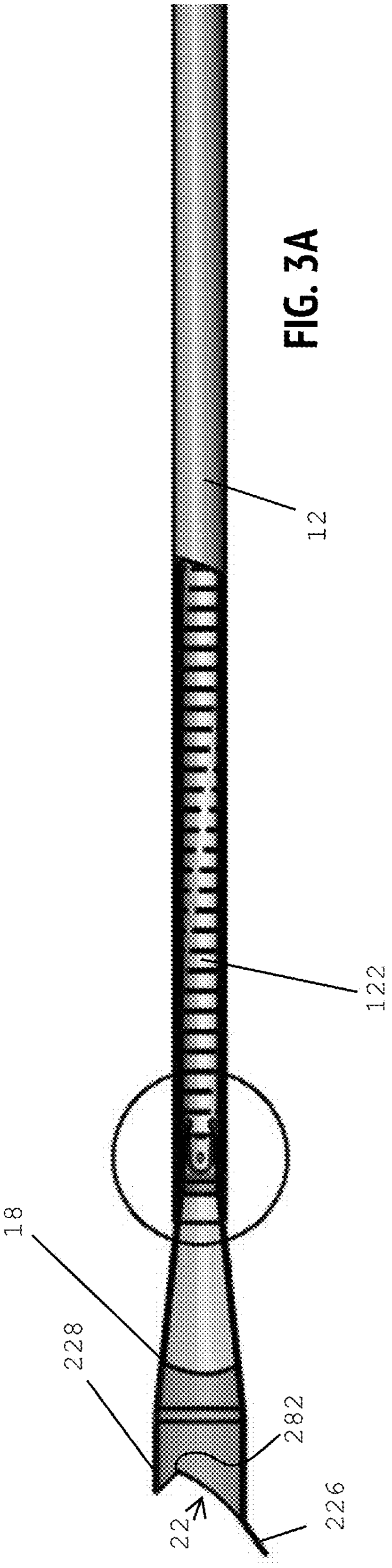
FIGS. 3A-D illustrate a flexible deployment tube with sidewall cutouts for manipulating the trap.
Figure 3B:
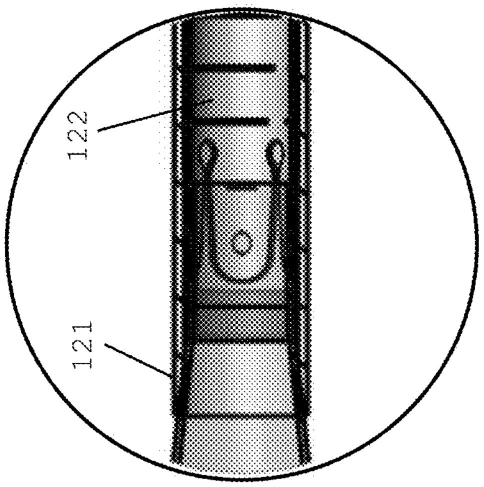
Figure 3C:
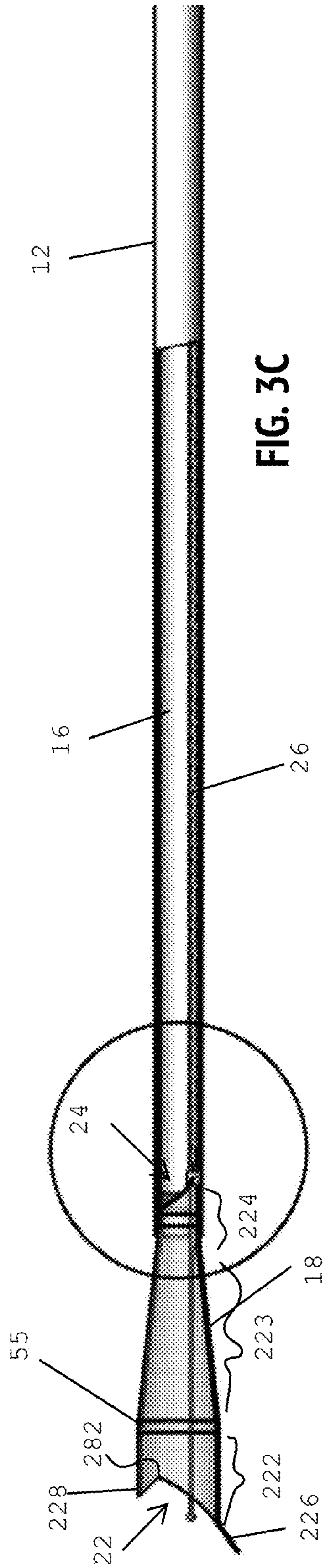

As shown in FIG. 3C, trap 18 may be shaped such that (i) a proximal portion 224 of the trap is cylindrical, (ii) a distal portion 222 of the trap is also cylindrical, and (iii) an intermediate section 223 of the trap flares (e.g. is frusto-conical) from the proximal section to the distal section to fluidically connect the distal section to the proximal section. In some implementations, shovel 226 (and optionally opposing shovel 228) extend distally from the distal section, to flare away from each other and from the longitudinal axis of trap 18.

Figures 2A, 2B, 2C, 2D:
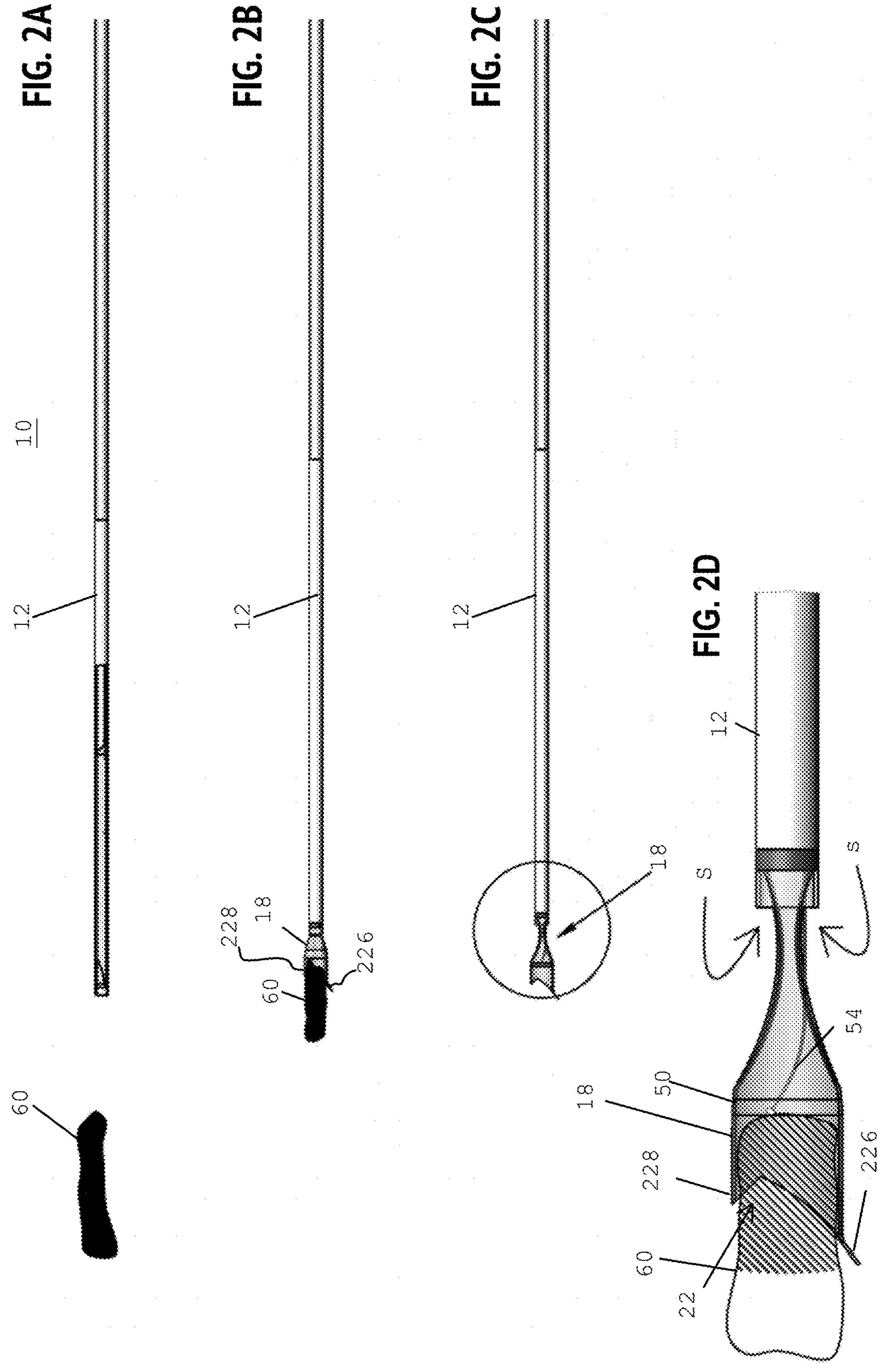
FIGS. 2A-D illustrate trap deployment at a clot (FIGS. 2A-B), clot plugging of the distal opening of the trap and subsequent trap collapse (FIG. 2C) leading to diversion of the suction path (FIG. 2D) and subsequent trap expansion.

At least one of shovel 226 and/or opposing shovel 228 may flare away from the other shovel and away from the longitudinal axis of trap 18. In some implementations, and as illustrated in FIGS. 2D-F, shovels 226 and 228 assist in the dislodgment of the embolus, e.g., by easing the embolus away from the walls of blood vessel, and/or by extending around the embolus such that distal opening 22 can envelope the embolus therewithin. In some implementations, only shovel 226 flares outwardly at the distal opening, (e.g., shovel 228, and the other wires at the outer perimeter of distal opening 22 do not flare outwardly). In some implementations, and as shown, only shovels 226 and 228 flare outwardly at the mouth, (e.g., the parts of distal opening 22 between the two shovels do not flare outwardly).

The proximal opening 24 can be circular in shape and perpendicular to the longitudinal axis of the catheter or oval in shape and tilted/angled (oblique) with respect to the longitudinal axis of the catheter. The proximal opening defines a trap-rim 242 (e.g. see FIG. 5B). Once trap 18 is exposed from catheter 12, proximal opening 24 opens directly into lumen 16, such that lumens 19 and 16 define a continuous lumen.

When collapsed within the catheter, the elongated trap is a narrow cylinder having a lumen of 0.9-4 mm in diameter (large enough for threading of a guidewire and/or micro-catheter and for suctioning of material).

According to one embodiment of the present invention, the elongated trap can be fabricated from metallic (e.g., stainless steel or NITINOL) or polymeric (e.g., PTFE) wires that are braided in alternating helical and counter-helical directions. The braid can be coated (completely or partially) with a polymer such as TPU, silicone or polyurethane to allow application of a vacuum to the lumen (internal volume) of the elongated trap. Such coating can be internal or external. An internal coating (e.g., a lining, and/or a membrane that covers the wires along the interior of the trap) is advantageous in that the non-coated outer surface does not fully seal against the blood vessel wall and completely arrest flow. In addition, an inner coating results in a smaller packing profile since the coating folds are tightly packed inside the braid construction.

The diameter of the wire can be between 0.02-0.25 mm while the braid angle between wires can range between 50-140 degrees. The elongated trap can be fabricated using a mandrel of suitable size by wrapping wires in an alternating helical pattern. For example, a single wire can be looped and the tails of the loop can be wrapped in a helical pattern around the mandrel so as to form a crisscrossing pattern in every wire (1×1 pattern) or crisscrossing pattern every 2 wires (2×1 pattern) along the length of the mandrel. Several wires (12-64) can be used to form the braided structure. An example of such braiding is provided in WO2019064306. The elongated trap can include wire loops at a distal end thereof (surrounding opening 22 of an expanded elongated trap 18). The wire loops form leaflets that provide axial support and decrease braid compression when the elongated trap contacts the clot (thereby minimizing an accordion effect that can occur when a braided structure is pushed against a clot). The wire loops also form a soft tip that minimizes vessel trauma during deployment. In some implementations, such wire loops define, or are disposed on, shovel 226.

The parameters and dimensions of the catheter and elongated trap depend on use and type of vessel. When used in ischemic stroke applications in an intra-cranial artery, the target artery size could vary between 1.5-4.5 mm. The elongated trap diameter should be at least slightly larger than the vessel diameter to arrest blood flow, and would therefore range between 2-7 mm. The length of the elongated trap can be long enough to support receiving long clots within the lumen, but short enough to allow deployment of the elongated trap by pushing it out of the catheter outer tube or by pulling in of a sheath.

Figure 3D:
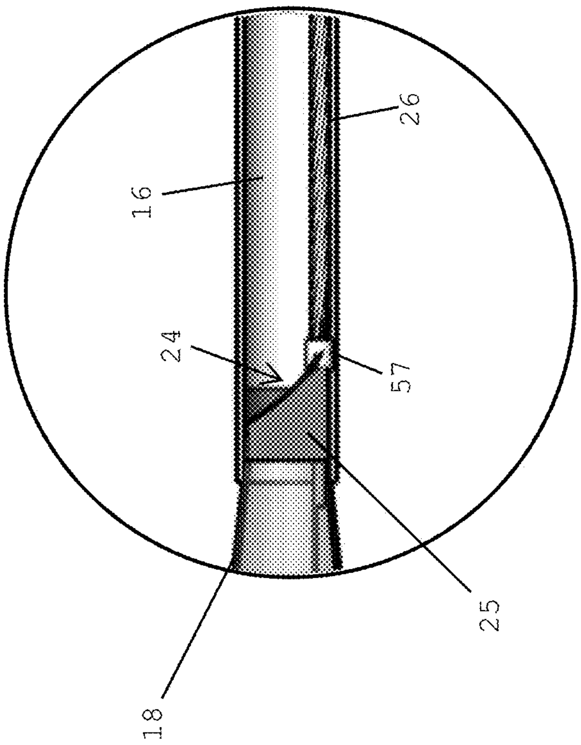

The catheter of the present system is used for delivering and deploying the trap. According to one embodiment of the present invention, the catheter system includes a single (outer) tube (that forms the catheter body/shaft) and the elongated trap. The elongated trap is positioned in a lumen of the outer tube and is pushed out for deployment via a wire/rod that is attached to the proximal end of the elongated trap. The wire is attached to the proximal end offset from the opening. In the case of a beveled proximal end, the wire is attached to the proximal-most tip of the bevel. The proximal portion 224 of the elongated trap includes an outer coating 25 (e.g., a bulky polymer coating, such as PEBAX, Pellethane, Carbothane, Nylon) that is selected capable of forming a tight seal with the inner wall of the outer tube and preventing the proximal opening from collapsing under the application of a suctioning force through the lumen of the outer tube. As is shown in FIG. 3D, the distal end of the coating can be tilted in order to minimize friction with the outer tube when the elongated trap is moved in and out of the outer tube.

The present catheter system can also include a source of suction (e.g., a syringe, a peristaltic pump) that can apply a suctioning force to the lumen (internal volume) of the elongated trap through a lumen of the outer tube. Thus, the outer tube that forms the catheter body functions in both sheathing the elongated trap and in providing a suctioning force to a lumen thereof. Such a configuration is advantageous in that it provides a relatively large diameter lumen through which suction can be applied to a relatively smaller proximal opening in the elongated trap.

The lumen of the outer tube forms a seal with the outer wall of the elongated trap when it is (at least partially) deployed out of the outer tube. To enhance such sealing, the proximal portion of the elongated trap includes a coating that forms a seal with the inner wall of the outer tube.

Application of a suctioning force through the lumen of the outer tube results in an equal suctioning force at distal opening 22 of the elongated trap when deployed. Employing an outer tube as a suctioning conduit ensures that any collapse of the elongated trap during suctioning breaks the seal between the outer tube lumen and the outer (coated) wall of the elongated trap. When this seal is breached, the suctioning force is at least partially diverted to the space between the outer wall of the elongated trap and the vessel wall, i.e., a space filled with biological fluid (e.g., blood). This results in a decrease of the suctioning force to the trap lumen and suctioning of fluid from the space between the trap and vessel wall and thus an equalization of pressures that leads to re-expansion of the elongated trap. This enables the trap to reseal against the outer tube lumen and restoration of full suction to the trap lumen. Such automatic 'pulsation' (which can repeat several times) can proximally advance material lodged in the distal opening of the trap.

While experimenting with several trap designs, the present inventors identified trap parameters that enable the above-described collapse-expansion cycle. For example, the trap can be conical in shape when expanded, with a diameter ratio of 2.3 between distal to proximal ends, a trap length 3 times that of the distal diameter, a coating thickness lower than 25 m and a radial collapse pressure of about 7 to 14 PSI.

Figure 6A:
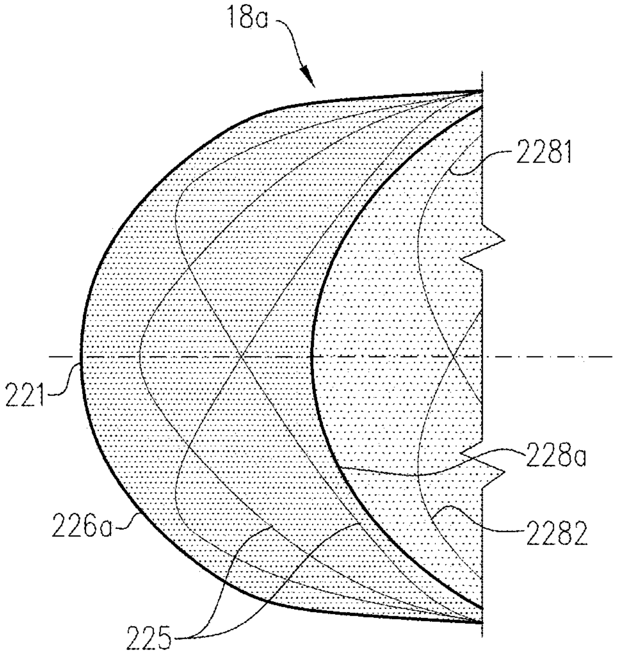
FIGS. 6A-B illustrate a trap in accordance with the teachings of the present invention.
Figure 6B:
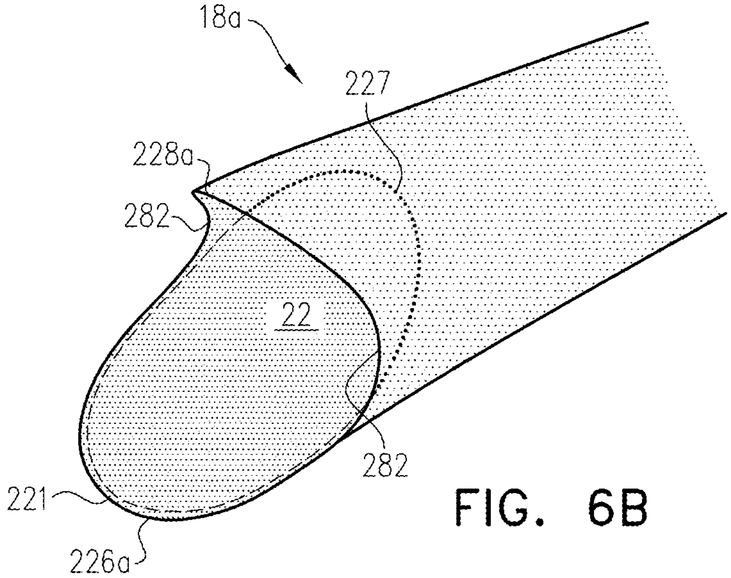

Reference is now made to FIGS. 6A-B, which illustrate a trap 18*a*, in accordance with some implementations. Trap 18*a* may be considered to represent optional features of trap 18 that are also visible in previous figures. Trap 18*a* may be considered to be a variant of trap 18. Trap 18*a* is formed from a set of braided wires 225 that define a shovel 226*a*, and an opposing shovel (e.g., beak) 228*a*. Opposing shovel 228*a* may be defined by at least two arc-wires 2281, 2282 of set 225 collectively, by each arc-wire forming an arc partway around the mouth, the arcs overlapping with each other, as shown.

The present system can further include at least one of: a pressure sensor (positioned in the catheter lumen, the lumen wall or at the pump), an element for restricting a bend radius of the trap so as to minimize kinking of the trap when navigating torturous anatomy, radio-opaque markers, and an emboli/object detection probe (positionable within the trap). These optional and individually applicable features are further described hereinunder with reference to the Figures.

Referring now to the drawings, FIGS. 1-4C illustrate the catheter system of the present invention which is referred to hereinunder as system 10.

System 10 includes a catheter body/shaft 12 that forms an outer tube 14 surrounding a lumen 16 (FIG. 1C). An elongated trap 18 that is used to trap (within a lumen 19) and/or retrieve a material or object from a biological vessel (e.g., artery) is positionable within lumen 16 and is deployable therefrom for retrieval. Trap 18 shown in the Figures is a coated braid structure 20 (FIG. 1C), however, alternative trap configurations such as polymer tubes, umbrella-like structures and the like are also envisaged herein.

Lumens 16 and 19 can be used to position system 10 over a guidewire, alternatively, the wall of lumen 16 can include a dedicated guidewire lumen. System 10 can be configured for standard over-the-wire or rapid exchange delivery. In the latter configuration, catheter body 12 can include a guidewire opening along its length.

Coated braid structure 20 can be constructed using several wires of varying degrees of rigidity. The braid forms a dense underlying network of thin wires to ensure substantial support to the encompassing polymeric coating. The integration of thick wires reinforces critical regions like the distal and proximal openings and strengthens the overall structure against the forces of suction. The ratio between the flexure rigidity of the thin and thick wires can be in the range of 1:2 to 1:3.

Coated braid structure 20 can include twenty-four 50 μm diameter Nitinol (NiTi) wires combined with four 64 μm diameter NiTi wires or sixteen 50 μm diameter NiTi wires combined with eight 64 μm diameter NiTi wires. DFT wires, with a braiding pattern of 1×1, with a 125° angle. The braid is internally coated with Polyurethane.

In the case of coated braid structure 20, proximal opening 24 can be surrounded by a radiopacity marker band 57 which be fixed by crimping it to the proximal end of trap 18 and a distal end of a wire/rod 26 used for deployment of trap 18 (further described hereinbelow). In addition, proximal portion of a braided elongated trap 18 can also include an external coating 25 (FIGS. 1C and 3D) of a polymer such as PEBAX, Pellethane, TPU or Nylon that prevents collapse of the proximal portion and opening 24 during application of a suction and also enhances sealing between the proximal portion and the inner walls of outer tube 14.

Catheter shaft 12 is selected of a length, diameter and flexibility suitable for the intended treatment location. Distal flexibility and proximal stiffness are used for trackability performances. A soft material jacket (PEBAX, polyurethane or polyamide composites with various durometer ratings) can be braided at a proximal portion and coiled at a distal portion to achieve distal flexibility (for navigating/positioning trap 18 in torturous anatomy) and proximal stiffness (for pushability).

FIG. 3A illustrates a flexible tube for pushing and pulling the trap inside the outer tube. FIG. 3B illustrates the interface of the flexible tube and the trap connection. The distal end of the flexible tube can be made from thin wall metal hypo tube 122 with a horizontal cutout allowing a flexible section, each cutout section may have different shapes for different flexibility sections (more flexible at distal, and pushability at proximal). The distal end of the flexible tube also has cutouts (horizontal and vertical) for connecting the trap to the flexible tube in various mechanical connections (e.g., adhesive or sewing) to create a strong connection that still maintains flexibility and kink resistance.

Catheter shaft 12 can be 130-150 cm long and 0.2-0.8 mm in outer diameter. Lumen 16 can be 0.9-2.0 mm in diameter and elongated trap can be 0.9-2.0 mm in diameter when collapsed within lumen 16 and 2.0-7.0 in diameter when deployed out of lumen 16. Trap 18 can be 10-30 mm in length.

System 10 can also include a pull wire for closing trap 18 following entrapment of, for example, a thrombus.

The pull wire extends from the proximal end through the lumen or wall of catheter body/shaft 12, the lumen of trap 18 (optionally in a helical pattern) and attaches to the distal end of trap 18 (e.g., in coated braid structure 20 to wire loops forming the distal end of the trap).

Closure can be via cinching (e.g., purse string) or via deflection (in the shovel configuration) by pulling the extended portions of the distal end (shovel tip) towards the base of the shovel. Alternatively, the shovel tip can be angled downward 10-30 degrees to disconnect the thrombus from the vessel wall by pulling the closure wire and lifting it thereby changing the height of the shovel.

Catheter body/shaft 12 of system 10 is attached to a handle 40 that includes port(s) 42 for attaching a syringe 44 (FIGS. 1A-B at I) or pump 46 and control unit 48 (FIGS. 1A-B at II) as well as mechanism(s) for deploying trap 18 and optionally a closure wire for closing the distal end of trap 18.

Syringe 44 or pump 46 are fluidly connected to lumen 16 and are capable of applying a suctioning pressure of −1 to −15 psi at a flow rate of 400-600 ml/min thereto (and thus to lumen 19 of deployed trap 18).

Syringe 44 is used manually by the operator while pump 46 (and attached/included control unit 48) is motor-driven (e.g., peristaltic pump). Pump 46 can be operated in an open or closed-loop configuration. In the latter case, control unit 48 can be connected to a pressure sensor positioned in lumen 16, the wall of lumen 16, pump 46 or port 42). Control unit 48 can include software for adjusting the suctioning force applied by pump 46 according to suction pressure readings from the pressure sensor.

For example, plugging of trap 18 under suction can lead to a rise in pressure detected by the pressure sensor that can lead to collapse of trap 18. To avoid or correct such collapse (in, for example, a configuration of system 10 that does not automatically compensate for such collapse via formation of an alternative suction path), the software of control unit 48 automatically lowers the suction pressure from pump 46 to re-expand trap 18. Once re-expanded (indicated by the pressure senor), the software can raise the suction pressure applied from pump 46 to the clot. Such suction 'pulsation' can enhance the ability of the system to retrieve the clot.

Figure 4A:
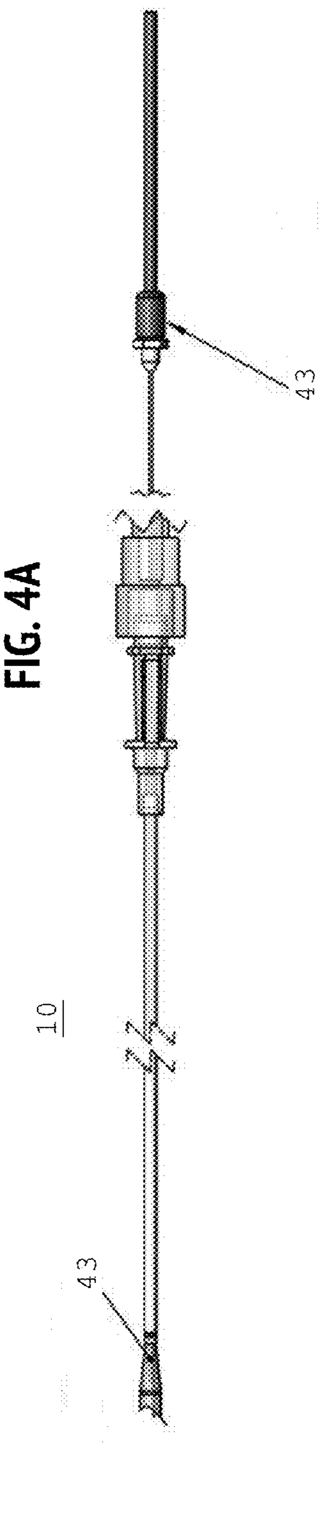
FIGS. 4A-C illustrate optional locations for a pressure probe (FIG. 4A), an element for restricting a bend radius of the trap (FIG. 4B) and an emboli/object detection sensor (FIG. 4C).

FIG. 4A illustrates two optional locations for pressure sensor 43. Pressure sensor 34 can be, for example, a strain gauge element embedded in, or attached to a wall of catheter body 12 or a pressure senor such as a piezoresistive or a differential pressure sensor positioned within syringe 44 or pump 46.

Handle 40 also includes a mechanism for deploying trap 18 (to the state shown in FIG. 1B). The mechanism can pull back catheter body/shaft 12 or push forward trap 18 via a wire/rod. The rod can be hollow and can include sidewall cutouts for flexibility.

For example, deployment of trap 18 can be carried out using a wire/rod 26 that is attached to a proximal end of trap 18 (FIG. 1C). Wire/rod 26 can be used to advance trap 18 out of lumen 16 by pushing forward wire/rod 26. Wire/rod 26 is connected to trap 18 at a location around proximal opening 24 (side, off center). In the case of a beveled proximal opening 24, wire/rod 26 is attached at a proximal-most point of the bevel (FIGS. 1C, 3D) via, for example crimping 57 or welding.

The proximal end of wire/rod 26 is attached to a handle 40 of system 10. Handle 40 includes a mechanism for pushing/pulling wire/rod 26 (and/or for pulling/pushing catheter body 12). Such a mechanism can be a rotating wheel, a slider button or a ratcheting trigger. The mechanism can provide a user with a visual or audible indication of deployment, and the extent of deployment, and prevents uncontrolled movement of the wire/rod due to the system's internal friction.

Figure 4B:
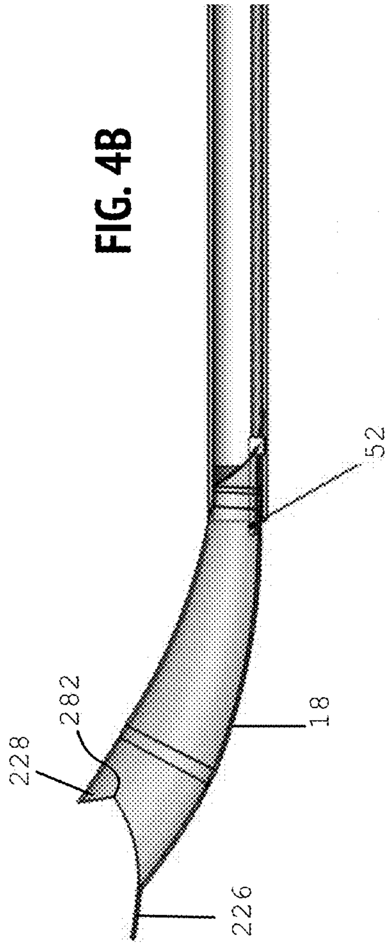
Figure 4C:
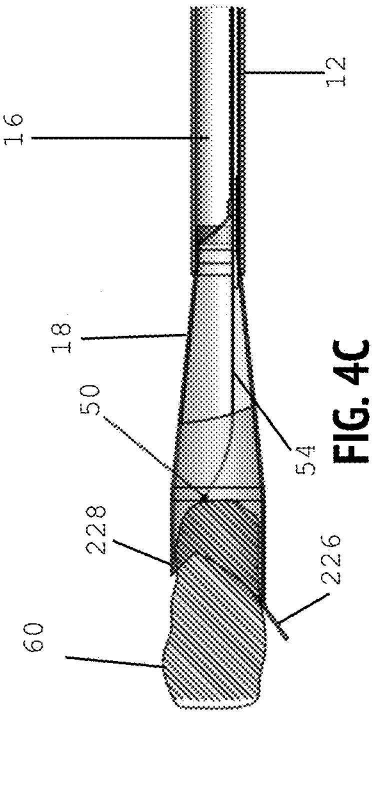

System 10 can further include a probe 50 for detecting the present of material/object at or within trap 18. FIGS. 2D and 4C illustrates one configuration of a such a probe 50 that is attached to a wire 54. In such a configuration, detection relies on the visualization of the radiopacity movement of the probe location in the fluoroscopy. In the case of a flexible wire with a marker band attached to its distal end, when the probe encounters material or an object it will deflect the probe toward the proximal side.

Since system 10 can be used in torturous vessels (e.g., brain vessels), positioning trap 18 in such vessels in order to collect a clot can lead to collapse or kinking of trap 18 when a radius of curvature of the vessel is relatively small (e.g., less than 1 mm). In such cases, trap 18 can include an element 52 for limiting/restricting the bend radius thereof. An example of such an element 52 is shown in FIG. 4B. Element 52 can be a flexural wire that passes through trap 18, which is end fixed proximal to trap 18, and his distal end is free. Element 52 has a flexural modulus larger than trap 18 which limits/restricts the bend radius of trap 18.

FIGS. 2A-D illustrate deployment of trap 18 from catheter body 12 and clot collection.

System 10 is delivered over a guidewire from an access site (e.g., trans-femoral, trans-radial) to clot 60 (FIG. 2A) under fluoroscopy imaging using standard over-the-wire or rapid exchange delivery techniques. Navigation of system 10 can be monitored using radio-opaque markers 55 attached to trap 18 (FIG. 3C) and/or catheter body 12.

Trap 18 is deployed next to clot 60 and suction is applied to lumen 19 through lumen 16. If clot 60 plugs distal opening 22 of trap 18 (as is shown in FIG. 2B), the suctioning force collapses trap 18 (FIG. 2C) due to the radial elasticity properties of trap 18 and leads to the formation of an alternative suction path (S in FIG. 2D) between the outer wall 62 of trap 18 and inner wall 64 of catheter body 12. Application of suction to the space formed between trap 18 and the wall of the vessel (not shown) leads to equalization of pressure between lumen 19 of trap 18 and the surrounding space and re-expands trap 18. This reforms the suction path to lumen 19 and redirects the suction force to clot 60. Such an automatic compensation mechanism effectively pulsates clot 60 into trap 18 (in a peristalsis-like action) and enables complete engulfment of clot 60.

Once retrieved, trap 18 with clot 60 can be pulled into catheter body 12 and the whole system can be removed from the body. Alternatively, clot 60 can be suctioned through lumen 16 and into syringe 44 or pump 46 and out of the body without removing system 10.

As used herein the term "about" refers to ±10%.

Additional objects, advantages, and novel features of the present invention will become apparent to one ordinarily skilled in the art upon examination of the following examples, which are not intended to be limiting.

In some implementations, rather than trap 18 being constructed from braided wires, in some implementations, the trap can be constructed from a continuous tubular funnel-shaped polymer (e.g., the polymer being shape-set to define the funnel-shape). In some implementations, the trap does not include a braided set of wires.

EXAMPLES

Reference is now made to the following example, which together with the above descriptions, illustrate the invention in a non-limiting fashion.

Prototype Testing

A prototype constructed in accordance with one embodiment of the present invention was bench tested for occlusion probability and aspiration efficacy.

Figure 5A:
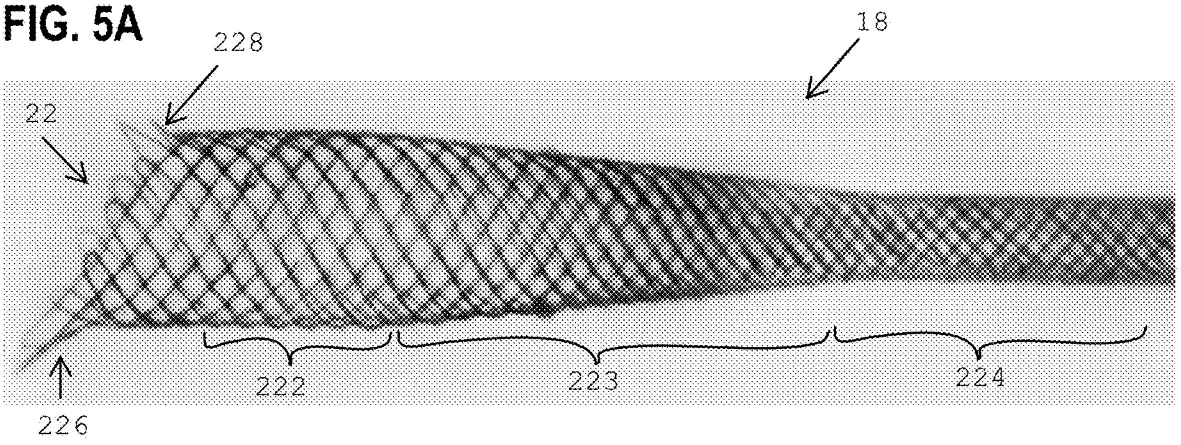
FIGS. 5A-B illustrate a prototype trap constructed in accordance with the teachings of the present invention.
Figure 5B:
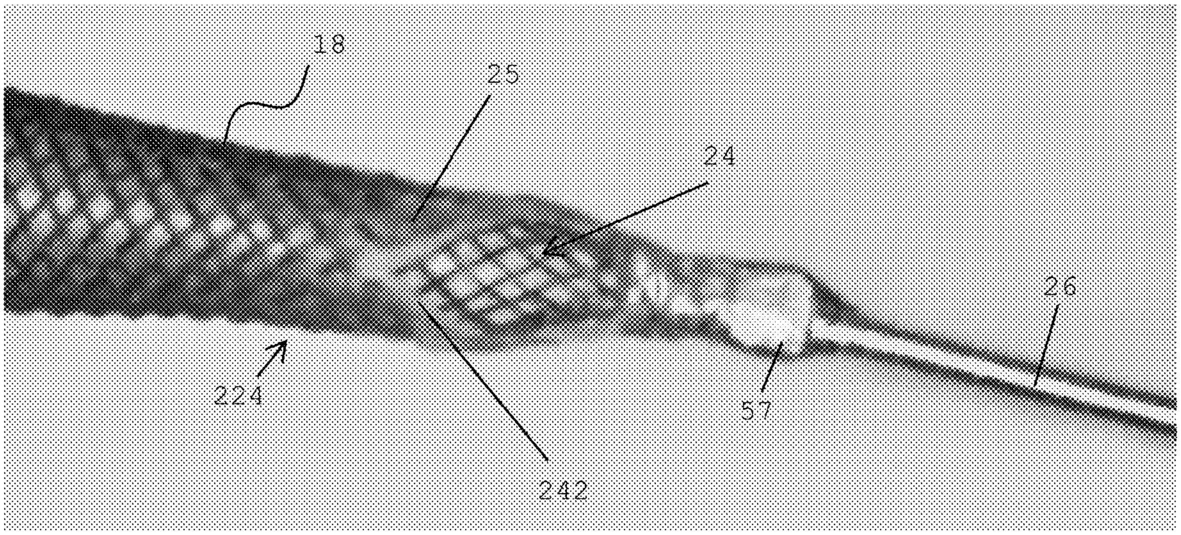

The prototype includes a single-tube catheter body and a self-expanding trap that was constructed from a wire braid coated with polyurethane (FIG. 5A-B). A deployment rod was connected off center to the proximal end of the trap and was used to deploy the trap out of the catheter lumen. The lumen of the catheter body served as an aspiration lumen with its inner wall sealing against the outer surface of the trap. Collapse of the trap during aspiration formed a secondary aspiration path between the lumen inner wall and the outer trap surface thereby leading to pressure equalization and restoration of trap shape. Such pressure equalization leads to a pulsation effect that facilitated aspiration of clots that plug the distal opening of the trap (a peristalsis-like effect).

The trap was beveled and open at both ends. FIG. 5A illustrates the expanded trap showing the beveled distal end. FIG. 5B illustrates the beveled proximal end with the rod connected (crimped) to the most proximal end of the beveled opening (point of attachment protrudes about 2 mm proximally).

Materials and Methods

A silicone replica model of the circle of Willis (manufactured by New England Center for Stroke Research, University of Massachusetts) was connected to a flow loop driven by a peristaltic pump delivering a flow rate of 140 ml/min. A soft elastic sheep blood clot was used to occlude the MCA trunk.

The MCA trunk was clamped distal to the thrombus to mimic the peripheral resistance. The system was fitted with a flow and pressure of 100 mm/Hg. A 6 Fr introducer catheter sheath was placed proximal to the occlusion at the ICA, through which the prototype was navigated proximal to the thrombus. The prototype was partially deployed and the self-expended trap expanded to the MCA diameter. Suction force (aspiration) was applied via a Vac-Lok 30 cc syringe connected to the catheter tube body.

Results

Navigation and unsheathing at the clot were successful and the clot was aspirated in one pass. The clot disintegrated into 2 fragments, the first occluded the trap but was fully aspirated due to the pulsation resulting from pressure equalization following trap collapse. Once the first fragment passed into the trap the second fragment followed. Although the clot disintegrated no distal embolization occurred due to trap sealing of the artery.

Conclusions

Prior art catheter designs often require multiple passes to retrieve clots that plug and collapse the catheter trap. The present prototype catheter showed great improvements in retrieving clots that can plug and collapse a trap by completely aspirating a soft clot into a syringe in a single pass.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. Apparatus for removing an obstruction from a blood vessel of a subject, the apparatus comprising:
- a flexible catheter, having:
  - a proximal part,
  - a distal part that is configured for transluminal advancement into the blood vessel, the distal part defining a catheter-rim, and
  - a lumen, extending from the proximal part to the catheter-rim; and
- a trap:
  - formed from a set of braided wires, and having a lining,
  - at a distal end of the trap, having an oval opening that is beveled such that the oval opening has a distal portion, and a proximal portion proximal from the distal portion,
  - having a beak, defined by wires of the set, and extending over the proximal portion of the oval opening, and
  - being biased to assume an expanded state in which the oval opening is wider than the catheter-rim, and
  - compressible within the lumen into a compressed state in which the oval opening is narrower than in the expanded state.

2. The apparatus according to claim 1, wherein the distal portion protrudes distally beyond the beak.

3. The apparatus according to claim 1, wherein the distal portion is longer than the beak.

4. The apparatus according to claim 1, wherein the distal portion and the beak meet at exactly two commissures.

5. The apparatus according to claim 1, wherein a proximal end of the trap opens directly into the lumen.

6. The apparatus according to claim 1, wherein the trap defines:
- a proximal trap-portion adjacent a proximal end of the trap that is generally cylindrical,
- a distal trap-portion adjacent the oval opening that is generally cylindrical, and
- an intermediate section, flaring from the proximal trap-portion to the distal trap-portion to fluidically connect the proximal trap-portion to the distal trap-portion.

7. The apparatus according to claim 1, wherein the beak is defined by two arc-wires of the set collectively, by each arc-wire forming an arc partway around the oval opening, the arcs overlapping with each other.

8. The apparatus according to claim 1, wherein a distal end of the distal portion defines a shovel, flaring outwardly and away from the beak.

9. The apparatus according to claim 8, wherein each of the shovel and the beak flare outwardly away from each other and from a longitudinal axis of the trap.

10. The apparatus according to claim 8, wherein the shovel is defined by distally extending wire loops that are angled outwardly.

11. The apparatus according to claim 1, wherein the wires of the set define:
- a first subset of wires having a first thickness, and
- a second subset of wires having a second thickness, the second thickness being less than the first thickness.

12. The apparatus according to claim 11, wherein wires of the first subset extend around a distal end of the trap to at least partially define the oval opening.

13. The apparatus according to claim 1, wherein the apparatus further comprises a flexible wire, attached to a proximal end of the trap, and extending proximally through the lumen of the catheter.

14. The apparatus according to claim 13, wherein:
- the proximal end is beveled, and
- the wire is attached to a proximal-most tip of the bevel.

15. The apparatus according to claim 13, wherein the apparatus further comprises a handle at the proximal part of the catheter, the handle comprising an actuator, operatively coupled to the flexible wire such that manual operation of the actuator progressively transitions the apparatus between (i) a delivery state in which the trap is in the compressed state within the catheter, and (ii) a deployed state in which the trap is in the expanded state and the oval opening is exposed from the distal part of the catheter.

16. The apparatus according to claim 15, wherein the actuator is a wheel, the actuator being operatable by rotating the wheel.

17. The apparatus according to claim 1 wherein:

the trap has a distal region that includes the distal end, and a proximal region proximal from the distal region, the trap is transitionable into the expanded state by being pushed distally such that, in the expanded state, the distal region is disposed outside of the lumen and the proximal region remains within the lumen, at the distal region, the wires are exposed at an exterior of the trap for imperfect sealing with a wall of the blood vessel while in the expanded state, and at the proximal region, the wires are coated in a bulky polymer coating, for tight sealing with an interior of the distal part of the catheter in the expanded state.

18. Apparatus for removing an obstruction from a blood vessel of a subject, the apparatus comprising:

a flexible catheter, having:

a proximal portion, a distal portion that is configured for transluminal advancement into the blood vessel, the distal portion having a catheter-rim, a lumen, extending from the proximal portion to the catheter-rim;

a trap:

formed from a set of braided wires covered in a covering, having a distal opening at a distal end of the trap, the distal opening defining:

a first shovel formed from wires of the set, the first shovel protruding distally, and an opposing shovel defined by wires of the set, the opposing shovel being opposite the first shovel and protruding distally, and at a proximal end of the trap, defining a proximal opening that is beveled and that defines a trap-rim, being biased to assume an expanded state in which the distal opening is wider than the proximal opening and the catheter-rim, and compressible within the lumen into a compressed state in which the distal opening is narrower than in the expanded state.

19. The apparatus according to claim 18, wherein the first shovel protrudes distally beyond the opposing shovel.

20. Apparatus for removing an obstruction from a blood vessel of a subject, the apparatus comprising:

a flexible catheter, having:

a proximal portion, a distal portion that is configured for transluminal advancement into the blood vessel, the distal portion having a catheter-rim, a lumen, extending from the proximal portion to the catheter-rim;

a trap:

formed from a set of braided wires covered in a covering, having a distal opening at a distal end of the trap, the distal opening defining:

a pair of commissures, and a pair of shovels that meet at the commissures, and extend distally from the commissures in divergence with each other, and at a proximal end of the trap, defining a proximal opening that defines a trap-rim, wherein the proximal opening is beveled, being biased to assume an expanded state in which the distal opening is wider than the proximal opening and the catheter-rim, and compressible within the lumen into a compressed state in which the distal opening is narrower than in the expanded state.

21. The apparatus according to claim 20, wherein one of the shovels of the pair protrudes distally beyond the other shovel of the pair.

* * * * *